US006287768B1

(12) United States Patent
Chenchik et al.

(10) Patent No.: US 6,287,768 B1
(45) Date of Patent: Sep. 11, 2001

(54) POLYMERIC ARRAYS AND METHODS FOR THEIR USE IN BINDING ASSAYS

(75) Inventors: Alex Chenchik, Palo Alto; Paul Siebert, Sunnyvale, both of CA (US)

(73) Assignee: Clontech Laboratories, Inc., Palo Alto, CA (US)

( * ) Notice: Subject to any disclaimer, the term of this patent is extended or adjusted under 35 U.S.C. 154(b) by 0 days.

(21) Appl. No.: 09/269,586

(22) PCT Filed: Jan. 6, 1999

(86) PCT No.: PCT/US99/00248

§ 371 Date: Mar. 3, 2000

§ 102(e) Date: Mar. 3, 2000

(87) PCT Pub. No.: WO99/35289

PCT Pub. Date: Jul. 15, 1999

Related U.S. Application Data

(63) Continuation of application No. 09/003,723, filed on Jan. 7, 1998, now Pat. No. 6,087,102.

(51) Int. Cl.$^7$ .............................. C12Q 1/68; C12P 19/34; C07H 21/04; C12M 1/34; C25B 11/00
(52) U.S. Cl. .................... 435/6; 435/91.1; 435/91.21; 435/283.1; 435/285.2; 435/287.2; 435/287.7; 536/23.1; 536/24.3; 536/24.31; 536/24.32; 536/24.33; 422/68.1; 204/600; 210/635
(58) Field of Search ...................... 435/4, 6, 7.1, 91.1, 435/91.21, 283.1, 285.1, 285.2, 287.2, 287.7, 288.4, 288.6; 536/23.1, 23.2, 23.4, 23.5, 24.3, 24.31, 24.32, 24.33, 25.32; 204/600; 422/68.1, 61, 62, 70, 71; 382/129; 210/634, 635, 656

(56) References Cited

U.S. PATENT DOCUMENTS

| | | | |
|---|---|---|---|
| 5,089,400 | * 2/1992 | Meyer | 435/69.51 |
| 5,242,828 | 9/1993 | Bergström et al. | 435/291 |
| 5,242,974 | 9/1993 | Holmes | 525/54.11 |
| 5,384,261 | 1/1995 | Winkler et al. | 436/518 |
| 5,403,901 | * 4/1995 | Heilmann et al. | 526/260 |
| 5,405,783 | 4/1995 | Pirrung et al. | 436/518 |
| 5,412,087 | 5/1995 | McGall et al. | 536/24.3 |
| 5,424,186 | 6/1995 | Fodor et al. | 435/6 |
| 5,429,807 | 7/1995 | Matson et al. | 422/131 |
| 5,436,327 | 7/1995 | Southern et al. | 536/25.34 |
| 5,445,934 | 8/1995 | Fodor et al. | 435/6 |
| 5,472,672 | 12/1995 | Brennan | 422/131 |
| 5,510,270 | 4/1996 | Fodor et al. | 435/518 |
| 5,527,681 | 6/1996 | Holmes | 435/6 |
| 5,529,756 | 6/1996 | Brennan | 422/131 |
| 5,545,531 | 8/1996 | Rava et al. | 435/6 |
| 5,554,501 | 9/1996 | Coassin et al. | 435/6 |
| 5,556,752 | 9/1996 | Lockhart et al. | 435/6 |
| 5,561,071 | 10/1996 | Hollenberg et al. | 437/1 |
| 5,599,672 | 2/1997 | Liang et al. | 435/6 |
| 5,624,711 | 4/1997 | Sundberg et al. | 427/261 |
| 5,639,603 | 6/1997 | Dower et al. | 435/6 |
| 5,658,734 | 8/1997 | Brock et al. | 435/6 |
| 5,700,637 | 12/1997 | Southern | 435/6 |
| 6,048,964 | * 4/2000 | Lee et al. | 530/350 |
| 6,074,822 | * 6/2000 | Henry | 435/6 |
| 6,087,102 | * 7/2000 | Chenchik et al. | 435/6 |

FOREIGN PATENT DOCUMENTS

| | | | |
|---|---|---|---|
| 0 742 287 A2 | 11/1996 | (EP) | C12Q/1/68 |
| 0 799 897 A1 | 10/1997 | (EP) | C12Q/1/68 |
| 93/17126 | 9/1993 | (WO) | C12Q/1/68 |
| 95/35505 | 12/1995 | (WO) | G01N/33/54 |

OTHER PUBLICATIONS

Watson et al Recombinant DNA 2nd Edition 1992 pp. 127–130.*
"Clontech Innovative Tools To Accelerate Discovery, Multiple Tissue Northern (MTN™)$^{Blots}$," *Clontech Laboratories, Inc.*
DeRisi, L. Joseph, et al., "Exploring The Metabolic And Genetic Control of Gene Expression On A Genomic Scale," *Science* (Oct. 24, 1997) vol. 278:680–686.
Glaser, Viki "Rosetta Inpharmatics Chips In," *Nature Biotechnology* (Oct. 15, 1997) vol. 15:937–938.
Hoheisel, D. Jorg "Oligomer–Chip Technology," *Tibtech* (Nov. 1997) vol. 15:465–469.
Lockhart, J. David, et al., "Expression Monitoring By Hybridization To High–Density Oligonucleotide Arrays," *Nature Biotechnology* (Dec. 1996) vol. 14: 1675–1680.
Marshall, Andrew et al., "DNA Chips: An Array Of Possibilities," *Nature Biotechnology* (Jan. 1998) vol. 16:27–31.
Pardee, B. Arthur "Complete Genome Expression Monitoring: The Human Race," *Nature Biotechnology* (Dec. 1997) vol. 15:1343–1344.
Ramsay, Graham "DNA Chips: State–Of–The–Art," *Nature Biotechnology* (Jan. 1998) vol. 16:40–44.
Saizieu, Antoine et al., "Bacterial Transcript Imaging By Hybridization Of Total RNA To Oligonucleotide Arrays," *Nature Biotechnology* (Jan. 1998) vol. 16:45–48.
Shalon, Dari et al., "A DNA Microarray System For Analyzing Complex DNA Samples Using Two–Color Fluorescent Probe Hybridization," *Genome Research* (1996) vol. 6:639–645.

(List continued on next page.)

*Primary Examiner*—Kenneth R. Horlick
*Assistant Examiner*—Jeffrey Siew
(74) *Attorney, Agent, or Firm*—Bret E. Field; Boziecevic, Field & Francis

(57) ABSTRACT

Arrays of polymeric targets stably associated with the surface of a rigid solid support are provided. In the subject arrays, the polymeric targets are arranged at least according to size. The polymeric targets of the subject arrays are generally biopolymeric compounds, e.g. nucleic acids and proteins, where ribonucleic acids and proteins are the preferred polymeric targets. The subject arrays find use in a variety of different applications, and are particularly suited for use in high through gene expression analysis applications.

19 Claims, 2 Drawing Sheets

OTHER PUBLICATIONS

Wodicka, Lisa et al., "Genome–Wide Expression Monitoring In Saccharomyces Cerevisiae," *Nature Biotechnology* (Dec. 1997) vol. 15:1359–1367.

Sambrook, J., "Molecular Cloning," *A Laboratory Manual.*, New York: Second Edition. Cold Spring Harbor Laboratory (1989) vol. 1:7.37–7.52.

Sambrook, J., "Molecular Cloning," *A Laboratory Manual.*, New York: Second Edition, Cold Spring Harbor Laboratory (1989) vol. 2:10.27–10.28.

Sambrook, J., "Molecular Cloning," *A Laboratory Manual.*, New York: Second Edition, Cold Spring Harbor Laboratory . (1989) vol. 3:18.47–18.71.

Sambrook et al., Molecular Cloning, A Laboratory Manual, (1989) pp. 9.31–9.43.*

Clontech Catalog (1995–1996) pp. 55–59, 140.*

Southern et al., J. Mol. Biol. (1975) 98:503–517.*

* cited by examiner

POLYMERIC ARRAYS AND METHODS FOR THEIR USE IN BINDING ASSAYS

CROSS-REFERENCE TO RELATED APPLICATIONS

This application claims priority to PCT application serial no. PCT/US99/00248 filed on Jan. 6, 1999; which application claims priority to U.S. application Ser. No. 09/003,723 filed Jan. 7, 1998 now U.S. Pat. No. 6,087,102, Jul. 11, 2000; the disclosures of which applications are herein incorporated by reference.

INTRODUCTION

1. Technical Field

The field of this invention is biopolymeric micro arrays.

2. Background of the Invention

"Biochips" or micro arrays of binding agents, such as oligonucleotides, have become an increasingly important tool in the biotechnology industry and related fields. These binding agent micro arrays, in which a plurality of binding agents are deposited onto a solid support surface in the form of an array or pattern, find use in a variety of applications, including drug screening, oligonucleotide sequencing, and the like. One important use of biochips is in the analysis of differential gene expression, where the expression of genes in different cells, normally a cell of interest and a control, is compared and any discrepancies in expression are identified. In such assays, the presence of discrepancies indicates a difference in the classes of genes expressed in the cells being compared. While such information is useful for the identification of the types of genes expressed in a particular cell or tissue type, it does not provide information regarding the size of specific gene products expressed by the cell.

To obtain such information, one has to rely on the standard blotting protocols, e.g. Northern blotting and analogous procedures. In such procedures, a complex mixture of potential target compounds is first size separated and then transferred to a flexible support. A probe capable of detecting the compound of interest in then contacted with the size separated targets. Following a positive probe/target binding event, detection of the bound probe yields information regarding the expression level (or abundance) and size of the target. While such blotting procedures are capable of providing size information, formats being used to date are not suitable for use in high throughput analysis.

Because information concerning types of genes expressed, level of expression and the size of the expressed products in a particular cell or tissue type are of interest in many applications, there is interest in the development of an array type device which can provide both types of information in a high throughput format.

Relevant Literature

Patents and patent applications describing arrays of biopolymeric compounds and methods for their fabrication include: U.S. Pat. Nos. 5,242,974; 5,384,261; 5,405,783; 5,412,087; 5,424,186; 5,429,807; 5,436,327; 5,445,934; 5,472,672; 5,527,681; 5,529,756; 5,545,531; 5,554,501; 5,556,752; 5,561,071; 5,599,895; 5,624,711; 5,639,603; 5,658,734; WO 93/17126; WO 95/11995; WO 95/35505; EP 742 287; and EP-799 897.

Patents and patent application describing methods of using arrays in various applications include: U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; WO 95/21265; WO 96/31622; WO 97/10365; WO 97/27317; EP 373 203; and EP 785 280.

Other references providing of micro array technology, including formats for arrays and methods of their use include: Lockhart et al., Nature Biotechnology (Dec. 1996) 14: 1675.

Clontech Catalogue, 97/98, (Clontech Laboratories, Inc. 1020 East Meadow Circle, Palo Alto, Calif. 94303) p. 81 describes premade Northern blots.

SUMMARY OF THE INVENTION

Arrays of polymeric targets stably associated with the surface of a rigid support are provided. In the subject arrays, the polymeric targets are arranged at least according to size of the targets. The polymeric targets are generally biopolymeric compounds, e.g. nucleic acids or proteins, and are preferably ribonucleic acids or proteins. The subject arrays find use in a variety of applications, and are particularly suited for use in high throughput gene expression analysis applications.

DEFINITIONS

Figure 1:
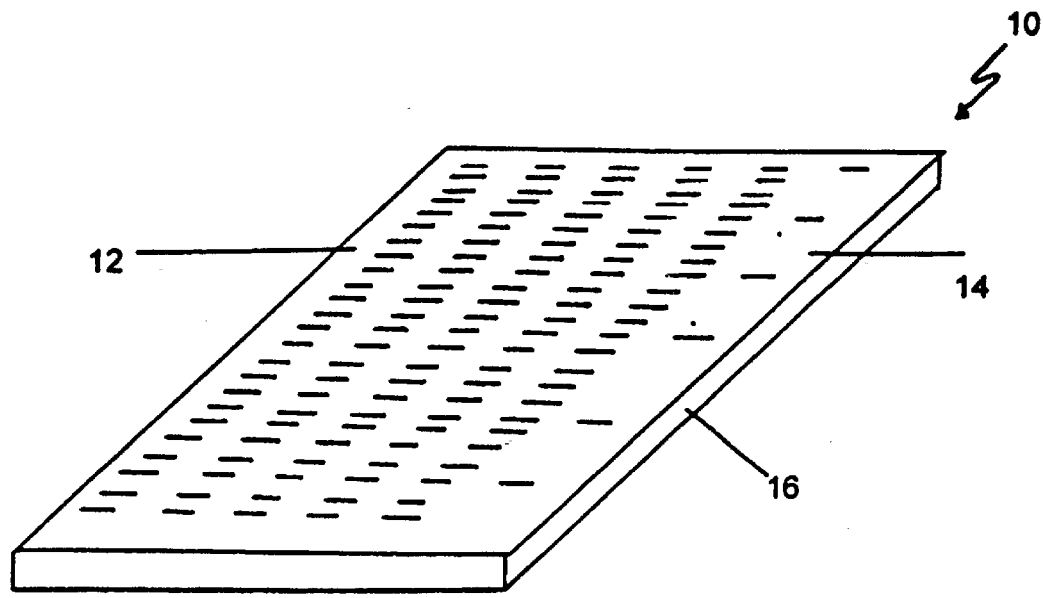
FIG. 1 provides a representation of an array according to the subject invention.

The term "peptide" as used herein refers to any compound produced by amide formation between a carboxyl group of one amino acid and an amino group of another group.

The term "oligopeptide" as used herein refers to peptides with fewer than about 10 to 20 residues, i.e. amino acid monomeric units.

The term "polypeptide" as used herein refers to peptides with more than 10 to 20 residues.

The term "protein" as used herein refers to polypeptides of specific sequence of more than about 50 residues.

The term "nucleic acid" as used herein means a polymer composed of nucleotides, e.g. deoxyribonucleotides or ribonucleotides.

The terms "ribonucleic acid" and "RNA" as used herein means a polymer composed of ribonucleotides.

The terms "deoxyribonucleic acid" and "DNA" as used herein means a polymer composed of deoxyribonucleotides.

The term "oligonucleotide" as used herein denotes single stranded nucleotide multimers of from about 10 to 100 nucleotides and up to 200 nucleotides in length.

The term "polynucleotide" as used herein refers to single or double stranded polymer composed of nucleotide monomers of generally greater than 100 nucleotides in length.

DESCRIPTION OF THE SPECIFIC EMBODIMENTS

Arrays of polymeric targets on a rigid support are provided, where the polymeric targets of the arrays are arranged at least with respect to size. The polymeric targets are typically biopolymers, such as nucleic acids or proteins. In preferred embodiments, the polymeric targets are either ribonucleic acids or proteins. The subject arrays find use in a variety of applications, and are particularly suited for use in high throughput gene expression analysis applications. In further describing the subject invention, the subject arrays will be described first, followed by a description of how the subject arrays can be prepared and a discussion of their use in representative binding assays.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

A critical feature of the subject invention is the array of polymeric targets arranged on a rigid support at least according to size. The polymeric targets of the subject arrays are typically biopolymeric, by which is meant that they are naturally occurring polymeric compounds or at least mimetics or analogues of naturally occurring polymeric compounds. Biopolymeric compounds of particular interest are ribonucleic acids, as well as deoxyribonucleic acid derivatives thereof generated through a variety of processes (usually enzymatic processes) such as reverse transcription, etc., e.g. cDNA amplified from RNA (both single and double stranded), cDNA inserts from cDNA libraries, and the like; and peptides, such as oligopeptides, polypeptides and proteins. In preferred embodiments, the polymeric targets are ribonucleic acids or proteins. Ribonucleic acids of interest as polymeric targets include total RNA, polyA$^+$RNA, polyA$^-$RNA, snRNA (small nuclear), hnRNA (heterogeneous nuclear), cytoplasmic RNA, pre mRNA, mRNA, cRNA (complementary), and the like. The RNA targets may be obtained or derived from naturally occurring biological sources, particularly mammalian sources and more particularly mouse, rat or human sources, where such sources include: fetal tissues, such as whole fetus or subsections thereof, e.g. fetal brain or subsections thereof, fetal heart, fetal kidney, fetal liver, fetal lung, fetal spleen, fetal thymus, fetal intestine, fetal bone marrow; adult tissues, such as whole brain and subsections thereof, e.g. amygdala, caudate nucleus, corpus callosum, hippocampus, hypothalamus, substantia nigra, subthalamic nucleus, thalamus, cerebellum, cerebral cortex, medula oblongata, occipital pole, frontal lobe, temporal lobe, putamen, adrenal cortex, adrenal medula, nucleus accumbens, pituitary gland, adrenal gland and subsections thereof, such as the adrenal cortex and adrenal medulla, aorta, appendix, bladder, bone marrow, colon, colon proximal with out mucosa, heart, kidney, liver, lung, lymph node, mammary gland, ovary, pancreas, peripheral leukocytes, placental, prostate, retina, salivary gland, small intestine, skeletal muscle, skin, spinal cord, spleen, stomach, testis, thymus, thyroid gland, trachae, uterus, uterus without endometrium; cell lines, such as breast carcinoma T-47D, colorectal adenocarcinoma SW480, HeLa, leukemia chronic myelogenous K-562, leukemia lymphoblastic MOLT-4, leukemia promyelocytic HL-60, lung carcinoma A549, lumphoma Burkitt's Daudi, Lymphoma Burkitt's Raji, Melanoma G361, teratocarcinoma PA-1, leukemia Jurkat; and the like. Proteins of interest as polymeric targets include naturally occurring proteins or fragments thereof, e.g. whole cell or tissue extracts, extracts of particular fractions thereof, such as cytoplasmic proteins, nuclear proteins, extracellular proteins and the like, where such proteins include: antibodies, receptors, hormones, and the like. Where the targets are derived from naturally occurring sources, such as mammalian tissues as described above, the targets may be derived from the same or different organisms, but will usually be derived from the same organism. In addition, the target samples arrayed on the plate can be derived from normal and disease or condition states of the same organism, like cancer, stroke, heart failure; aging, infectious diseases, inflammation, exposure to toxic, drug or other agents, conditional treatment, such as heat shock, sleep deprivation, physical activity, etc., different developmental stages, and the like.

In a preferred embodiment, the target is total RNA or polyA$^+$RNA.

The target, e.g. RNA, may be used directly from its source when presence in relatively great abundance or amplified, e.g. by PCR transcription or cloning procedures, where necessary, e.g. when relatively rare, such as RNA from rare tissue, etc.

In the subject arrays, the targets are stably associated with the surface of a rigid support. By stably associated is meant that the targets maintain their position relative to the rigid support under hybridization and washing conditions. As such, the targets can be non-covalently or covalently stably associated with the rigid support surface. Examples of non-covalent association include non-specific adsorption, specific binding through a specific binding pair member covalently attached to the support surface, and entrapment in a matrix material, e.g. a hydrated or dried separation medium, which presents the target in a manner sufficient for binding, e.g. hybridization, to occur. Examples of covalent binding include covalent bonds formed between the target and a functional group present on the surface of the rigid support, e.g. -OH, where the functional group may be naturally occurring or present as a member of an introduced linking group, as described in greater detail below.

As mentioned above, the array is present on a rigid substrate. By rigid is meant that the support is solid and does not readily bend, i.e. the support is not flexible. Examples of solid materials which are not rigid supports with respect to the present invention include membranes, flexible plastic films, and the like. As such, the rigid substrates of the subject arrays are sufficient to provide physical support and structure to the polymeric targets present thereon under the assay conditions in which the array is employed, particularly under high throughput handling conditions.

The rigid substrates upon which the subject patterns of targets are presented in the subject arrays may take a variety of configurations ranging from simple to complex, depending on the intended use of the array. Thus, the substrate could have an overall slide or plate configuration, such as a rectangular or disc configuration, where an overall rectangular configuration, as found in standard microtiter plates and microscope slides, is preferred. Generally, the length of the rigid substrates will be at least about 1 cm and may be as great as 40 cm or more, but will usually not exceed about 30 cm and may often not exceed about 15 cm. The width of rigid substrate will generally be at least about 1 cm and may be as great as 30 cm, but will usually not exceed 20 cm and will often not exceed 10 cm. The height of the rigid substrate will generally range from 0.01 mm to 10 mm, depending at least in part on the material from which the rigid substrate is fabricated and the thickness of the material required to provide the requisite rigidity.

The rigid substrates of the subject arrays may be fabricated from a variety of materials. The materials from which the substrate is fabricated should ideally exhibit a low level of non-specific binding of probe during hybridization or specific binding events. In many situations, it will also be preferable to employ a material that is transparent to visible and/or UV light. Specific materials of interest include: glass; plastics, e.g. polytetrafluoroethylene, polypropylene, polystyrene, polycarbonate, and blends thereof, and the like; metals, e.g. gold, platinum, and the like; etc.

The rigid substrate of the subject arrays comprise at least one surface on which a pattern of target molecules is present, where the surface may be smooth or substantially planar, or have irregularities, such as depressions or elevations. The surface on which the pattern of targets is presented may be modified with one or more different layers of compounds that serve to modulate the properties of the surface in a desirable manner. Such modification layers, when present, will generally range in thickness from a monomolecular thickness to about 1 mm, usually from a monomolecular thickness to about 0.1 mm and more usually from a monomolecular thickness to about 0.001 mm. Modification layers of interest include: inorganic and organic layers such as metals, metal oxides, polymers, small organic molecules and the like. Polymeric layers of interest include layers of: peptides, proteins, polynucleic acids or mimetics thereof, e.g. peptide nucleic acids and the like; polysaccharides, phospholipids, polyurethanes, polyesters, polycarbonates, polyureas, polyamides, polyethyleneamines, polyarylene sulfides, polysiloxanes, polyimides, polyacetates, and the like, where the polymers may be hetero- or homopolymeric, and may or may not have separate functional moieties attached thereto, e.g. conjugated.

The concentration of the target positions on the surface of the support is selected to provide for adequate sensitivity of binding events with a probe carrying a variety of different labels, where the concentration will generally range from about 1 to 100, usually from about 5 to 50 and more usually from about 10 to 30 ng/mm$^2$. As summarized above, the subject arrays comprise a plurality of different polymeric targets, where the number of targets is at least 5, usually at least 8, and may be much higher. In some embodiments, the arrays have at least 10 distinct spots, usually at least about 20 distinct spots, and more usually at least about 50 distinct spots, where the number of spots may be as high as 10,000 or higher, but will usually not exceed about 5,000 distinct spots, and more usually will not exceed about 3,000 distinct spots. The density of the spots on the solid surface in certain embodiments is at least about 5/cm$^2$ and usually at least about 10/cm$^2$ but does not exceed about 1000/cm$^2$, and usually does not exceed about 500/cm$^2$, and more usually does not exceed about 300/cm$^2$.

A critical feature of the subject arrays is the target members of the array are arranged on the surface of the solid support at least with respect to size, by which is meant that the organization of the pattern of targets on the support is at least reflective of the size of each of the member targets in the array. With respect to the arrangement according to size, the targets could be arranged in a continuous or discontinuous size format. By continuous is meant that in the pattern of targets in the array, each successive position in the array, such as a successive position in a lane of targets where the pattern has a lane configuration, comprises target molecules of the same molecular weight. By discontinuous format is meant that each position in the pattern, e.g. band in a lane, represents a fraction of target molecules derived from the original source, e.g. a fraction spanning a size range of from $1 \cdot 10^4$ to $1.2 \cdot 10^4$ daltons. As such, in the discontinuous format, each target position in the pattern will comprise a fraction of targets from the original sample, where the targets in each fraction will have a molecular weight within the range determined during the preparation of the fractions, as described in greater detail below.

The pattern of targets may take on a variety of configurations as long as each position in the array represents a unique size, where size means a unique molecular weight or range of molecular weights, as described above, depending on whether the array has a continuous or discontinuous format. Preferably, the pattern will be in the form of at least one lane of each individual target positions, i.e. as a linear row on the surface of the rigid substrate. The subject arrays may comprise a single lane or a plurality of lanes on the surface of the substrate, where when a plurality of lanes are present, the number of lanes will usually be at least 2 but less than 200, more commonly more than 5 but less than 100, and most commonly more than 8 but less than 80.

Each array may comprise targets obtained from the same source, e.g. the same tissue, such as one or more lanes representing a large proportion of the total mRNA from a tissue source, or comprise targets from different sources, e.g. different tissues from the same organism, i.e. mouse, rat, or human, or disease and normal tissue obtained from the same original host source or different host sources, where when targets from different sources are presented, each individual pattern, e.g. lane, on the surface of the support will comprise targets from the same source, i.e. the patterns will be homogeneous with respect to their source. Therefore, in such embodiments the surface of the rigid substrate will present a plurality of patterns of target molecules derived from different sources, e.g. tissues, wherein the targets in each array, e.g. lane, are arranged according to size, either continuously or discontinuously, as described above. See FIG. 1. In FIG. 1, array 10 consists of a solid support 16 on the surface of which is presented a pattern 12 of polymeric targets arranged according to size. A size marker lane 14 is also provided.

Figure 2:
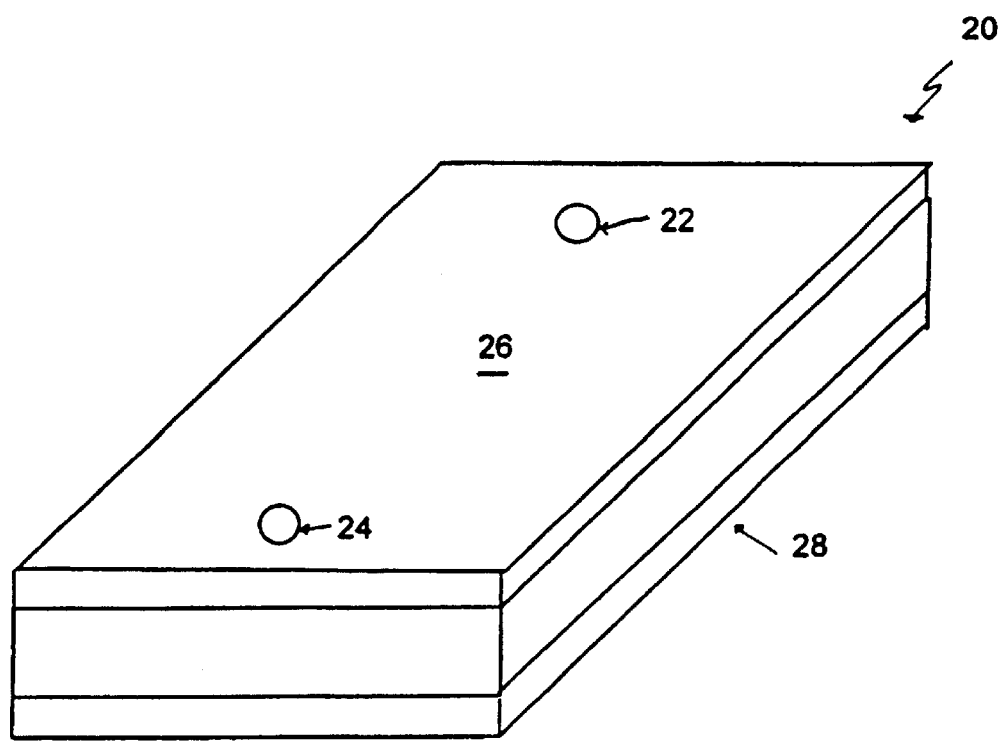
FIG. 2 provides a representation of a first embodiment of a "biochip" according to the subject invention.
Figure 3:
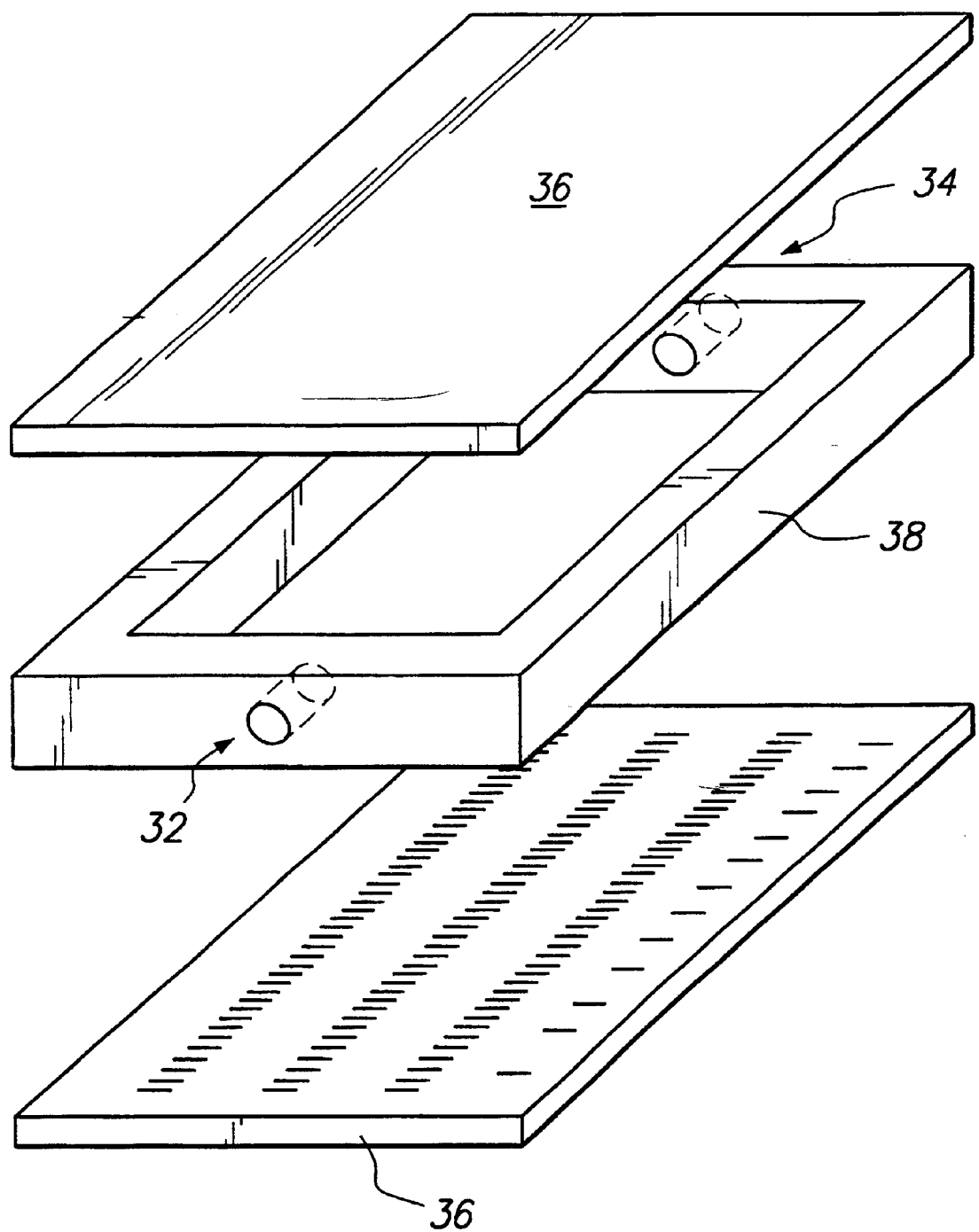
FIG. 3 provides a representation of a second embodiment of a "biochip" according to the subject invention.

The arrays of the subject invention may be used directly in binding assays using well known technologies, e.g. contacting with probe in a suitable container, under a coverslip, etc, or may be incorporated into a structure that provides for ease of analysis, high throughput, or other advantages, such as in a biochip format, a multiwell format and the like. For example, the subject arrays could be incorporated into a biochip type device in which one has a substantially rectangular shaped cartridge comprising fluid entry and exit ports and a space bounded on the top and bottom by substantially planar rectangular surfaces, wherein the array is present on one of the top and bottom surfaces. A representative biochip device in assembled form is shown in FIG. 2 and FIG. 3. In FIG. 2, biochip device 20-comprises top and bottom planar plates 26 separated by a spacer wall 28 in manner that provides for a substantially enclosed chamber, inside of which is positioned an array according to the subject invention. Reagent inlet port 22 provides for reagent introduction into the chamber and outlet port 24 provides for fluid outlet. FIG. 3 shows a dissambled form, where the pattern of polymeric targets are arranged according to size and a size marker is also present.

Alternatively, the subject arrays could be incorporated into a high throuput or multiwell device, wherein each array is bounded by raised walls in a manner sufficient to form a reaction container wherein the array is the bottom surface of the container. Such high throuput devices are described in U.S. patent application Ser. No. 08/974,298, now abandoned, the disclosure of which is herein incorporated by reference. Generally in such devices, the devices comprise a plurality of reaction chambers, each of which contains the array on the bottom surface of the reaction chamber. By plurality is meant at least 2, usually at least 4 and more usually at least 24, where the number of reaction chambers may be as high as 96 or higher, but will usually not exceed 100. The volume of each reaction chamber may be as small as 10 µl but will usually not exceed 500 µl.

The subject arrays may be prepared as follows. The rigid substrate or support can be fabricated according to known procedures, where the particular means of fabricating the support will necessarily depend on the material from which it is made. For example, with polymeric materials, the support may be injection molded, while for metallic materials, micromachining may be the method of choice. Alternatively, rigid supports such as glass, plastic, or metal sheets can be purchased from a variety of commercial sources and used. The surface of the support may be modified to comprise one or more surface modification layers, as described above, using standard deposition techniques.

The next step in the preparation process is to prepare the pattern of target molecules and then stably associate the resultant size separated target molecules with the surface of the rigid support. The complex source of target molecules may be obtained from its naturally occurring physiological source using standard techniques. Protocols for isolating nucleic acids, proteins and their fractions from cells, tissues, organs and whole organisms are described in: Maniatis et al., Molecular Cloning: A Laboratory Manual (Cold Spring Harbor Press)(1989); Scope R., Protein Purification. Principle and Practice (Springer-Verlag)(1994); and Deutscher, Guide to Protein Purification (Academic Press)(1990). Such methods typically involve subjection of the original biological source to one or more of tissue/cell homogenization, nucleic acid/protein extraction, chromatography, centrifugation, affinity binding and the like. Target molecule preparation can further include one or more treatments designed to provide for one or more of the following: improved size separation of the target the molecules; more stable association with the surface of the rigid support; and better hybridization and detection. Such treatments will necessarily depend on the nature of the target molecules being prepared, but may include one or more of: reverse transcription; nuclease treatment; protease digestion; in vitro transcription; in vitro translation; DNA amplification; enzymatic or chemical modification of RNA or proteins, such as the introduction of functional moieties, such as biotin, digoxigenin, fluorescent moieties, antigens, chelator groups, chemically active or photoactive groups, etc.; and the like.

Following preparation of the complex mixture of the target molecules, the mixture will be size separated, where size separation can be in a continuous or discontinuous manner, and stably associated with the surface of the rigid support. For size separation of the mixture of target molecules in a continuous manner, the complex target mixture may be electrophoretically separated in a separation medium under conditions sufficient to substantially resolve each mixture constituent by weight or size, such that each resultant group of molecules has the same molecular weight or size. Any convenient electrophoretic technique may be employed to achieve the desired size separation, and a variety of suitable separation mediums are known and available, such as linear and crosslinked polymeric gel mediums, including: polyacrylamide and derivatives thereof; agarose and derivatives thereof; polyacrylamide/ agarose composite gels; poly-N-acryloyl-tris gel; polysaccharides; hydroxyethylcellulose; poly-N,dimethyl acrylamide; polyethyleneoxide; polyethylene oxide-polypropylene oxide block copolymers (eg. as sold under the trademark Pluronic™) and the like.

The separation medium may conveniently be used as a matrix for holding the size separated target molecules in stable position relative to the surface of the rigid support (i.e. an entrapment matrix). In such embodiments, the size separation may be carried out in a separation medium that is supported by the rigid support, where the separation medium may be covalently or non-covalently attached to the rigid support surface. In another embodiment the size separation may be carried out in a separation medium that is bounded in a space between rigid planar surfaces, e.g. rectangular glass plates separated from each other by a spacer. In such embodiments, the separation medium that subsequently serves as a matrix for holding the size separated molecules on the surface of the rigid support may be maintained as a gel or dried, where when the gel is dried, care will be taken to ensure the cracking of the gel does not occur. As such, the entrapment matrix will, when present, generally range in thickness from about 0.01 to 10 mm, usually from about 0.05 to 5 mm and more usually from about 0.1 to 2 mm. To further ensure stable association with the surface of the rigid support in the separation medium (i.e. entrapment matrix) the target molecules may be crosslinked with the components of the separation matrix according to methods known in the art, i.e. photo and/or chemical crosslinking.

Alternatively, the molecules may be size separated in a continuous fashion and then transferred to the rigid support. Transfer can be accomplished in a number of different manners, where the particular protocol employed will necessarily depend on the separation procedure used for size separation of the target molecules. Methods for transfer of the size separated molecules to the support surface include: electrophoresis; blotting; passive diffusion; and the like. In such embodiments, the surface of the rigid support and/or the target molecules will be selected and or pretreated, as described above, to provide for stable association of the deposited pattern of target molecules with the support surface. For example, where the pattern of target molecules is to be stably associated with the rigid support surface through covalent bonds, a rigid support comprising appropriate functional moieties, e.g. —$NH_2$ for nucleic acids, will be employed. Conversely, where stable association is to be achieve through specific binding pair interaction, steps will be taken to ensure that the appropriate specific binding pair members, e.g. avidin, streptavidin, antibodies, ligands, oligo dT, and the like, are present on the support surface. In another embodiment, stable association is achieved through non-specific interactions (e.g. electrostatic, hydrophobic, hydrophilic, hydrogen bond, and the like) between functional moieties of the target molecules and functional moieties present on the rigid support surface.

For discontinuous size separated patterns, the initial complex mixture of target molecules will be separated into a plurality of fractions, wherein each fraction consists of a range of molecular weights, i.e. the member compounds of each fraction will fall within a range of molecular weights, where the magnitude of the range in each fraction will be at least $10^3$ daltons and usually at least $2 \cdot 10^3$ daltons and may be as large as $5 \cdot 10^3$ daltons or larger, but will usually not exceed about $10^6$ daltons and more usually will not exceed about $10^5$ daltons. Fractionation of the initial complex mixture of target molecules may be accomplished using any convenient technique, where such techniques include: electrophoresis, including preparative gel, capillary, and the like; low pressure FPLC or HPLC chromatography, such as size exclusion, ion exchange, ion pair, hydrophobic chromatography; ultra centrifugation; FACS sorting molecules of molecules by size; and the like. The number of fractions produced from the initial complex mixture will be at least 10, usually at least 20 and more usually at least 30, where the number will generally not exceed 1000 and usually will not exceed 500 and more usually will not exceed 200. The resultant fractions may be deposited on the rigid support surface using any convenient means, such as by using an "ink-jet" device, mechanical deposition, pipetting and the like. After deposition of material onto the solid surface, it can be treated in different ways to provide for stable association of the target, blockage of non-specific binding sites, removal of unbound target, and the like. As with preparation of arrays in which the pattern is based on a continuous separation format, steps are taken to ensure that the pattern of fractions of target molecules placed on the rigid support surface is stably attached thereto, where such steps are described above.

Following stable placement of the pattern of target molecules on the support surface, the resultant array may be used as is or incorporated into a biochip, multiwell or other device, as describe above, for use in a variety of binding applications.

The subject arrays or devices into which they are incorporated may conveniently be stored following fabrication for use at a later time. Under appropriate conditions, the subject arrays are capable of being stored for at least about 6 months and may be stored for up to one year or longer. The subject arrays are generally stored at temperatures between about −20° C. to room temperature, where the arrays are preferably sealed in a plastic container, e.g. bag, and shielded from light.

Applications in which the subject arrays find particular use are expression analysis applications. Such applications generally involve the following steps: (a) preparation of probe; (b) contact of probe with the array under conditions sufficient for probe to bind with corresponding target, e.g. by hybridization or specific binding; (c) removal of unbound probe from the array; and (d) detection of bound probe. Each of these steps will be described in greater detail below.

How the probe is prepared will necessarily depend on the specific nature of the probe, e.g. whether the probe is nucleic or peptidic. For nucleic acid probes, the probes may be ribo- or deoxyribonucleotides, as well as hybridizing analogues or mimetics thereof, e.g. nucleic acids in which the phosphodiester linkage has been replaced with a substitute linkage, such as a phosphorothioate, methylimino, methylphosphonate, phosphoramidite, guanidine and the like;and nucleic acids in which the ribose subunit has been substituted, e.g. hexose phosphodiester, peptide nucleic acids; locked nucleic acids; and the like. The probe will have sufficient complementarity to its target to provide for the desired level of sequence specific hybridization. Where the probe is a nucleic acid, the length of the probe will generally range from about 10 to 2000 nt, where oligonucleotide probes will generally range in length from about 15 to 100 nt and polynucleotide probes will generally range in length from about 100 to 1000 nt, where such probes may be single or double stranded, but will usually be single stranded. The nucleic acid probes finding use in the subject methods may be synthesized using known chemical or enzymatic synthesis technologies, cloning procedures or obtained from a natural source.

Peptidic probes that find use in the subject invention include: antibodies, e.g. polyclonal, monoclonal, and binding fragments thereof; peptides with high affinity to the target, as well as analogues and mimetics thereof; ligands, receptors, and the like. As with the nucleic probes, peptidic probes may be obtained from naturally occurring sources or synthesized using available technologies.

Generally, the probe molecule will be labeled to provide for detection in the detection step. By labeled is meant that the probe comprises a member of a signal producing system and is thus detectable, either directly or through combined action with one or more additional members of a signal producing system. Examples of directly detectable labels include isotopic and fluorescent moieties incorporated into, usually covalently bonded to, a moiety of the probe, such as a nucleotide monomeric unit, e.g. dNMP of the primer, or a photoactive or chemically active derivative of a detectable label which can be bound to a functional moiety of the probe molecule. Isotopic moieties or labels of interest include $^{32}$P, $^{33}$P, $^{35}$S, $^{125}$I, and the like. Fluorescent moieties or labels of interest include coumarin and its derivatives, e.g. 7-amino-4-methylcoumarin, aminocoumarin, bodipy dyes, such as Bodipy FL, cascade blue, fluorescein and its derivatives, e.g. fluorescein isothiocyanate, Oregon green, rhodamine dyes, e.g. Texas red, tetramethylrhodamine, eosins and erythrosins, cyanine dyes, erg. Cy3 and Cy5, macrocyclic chelates of lanthanide ions, e.g. quantum dye™, fluorescent energy transfer dyes, such as thiazole orange-ethidium heterodimer, TOTAB, etc. Also of interest are nanometer sized particle labels detectable by light scattering, e.g. "quantum dots." Labels may also be members of a signal producing system that act in concert with one or more additional members of the same system to provide a detectable signal. Illustrative of such labels are members of a specific binding pair, such as ligands, e.g. biotin, fluorescein, digoxigenin, antigen, polyvalent cations, chelator groups and the like, where the members specifically bind to additional members of the signal producing system, where the additional members provide a detectable signal either directly or indirectly, e.g. antibody conjugated to a fluorescent moiety or an enzymatic moiety capable of converting a substrate to a chromogenic product, e.g. alkaline phosphatase conjugate antibody; and the like. Additional labels of interest include those that provide for signal only when the probe with which they are associated is specifically bound to a target molecule, where such labels include: "molecular beacons" as described in Tyagi & Kramer, Nature Biotechnology (1996) 14:303 and EP 0 070 685 B1. Other labels of interest include those described in U.S. Pat. No. 5,563,037; WO 97/17471 and WO 97/17076.

The next step in the subject method is to contact the probe with the array under conditions sufficient for binding between the probe and the target of the array. For example, where the probe and target are nucleic acids, the probe will be contacted with the array under conditions sufficient for hybridization to occur between the probe and target, where the hybridization conditions will be selected in order to provide for the desired level of hybridization specificity. For peptidic probes, conditions will be selected to provide for specific binding between the probe and its target.

Contact of the array and probe involves contacting the array with an aqueous medium comprising the probe. Contact may be achieved in a variety of different ways depending on specific configuration of the array. For example, where the array simply comprises the pattern of size separated targets on the surface of a "plate-like" rigid substrate, contact may be accomplished by simply placing the array in a container comprising the probe solution, such as a polyethylene bag, small chamber, and the like. In other embodiments where the array is entrapped in a separation media bounded by two rigid plates, the opportunity exists to deliver the probe via electrophoretic means. Alternatively, where the array is incorporated into a biochip device having fluid entry and exit ports, the probe solution can be introduced into the chamber in which the pattern of target molecules is presented through the entry port, where fluid introduction could be performed manually or with an automated device. In multiwell embodiments, the probe solution will be introduced in the reaction chamber comprising the array, either manually, e.g. with a pipette, or with an automated fluid handling device.

Contact of the probe solution and the targets will be maintained for a sufficient period of time for binding between the probe and the target to occur. Although dependent on the nature of the probe and target, contact will generally be maintained for a period of time ranging from about 10 min to 24 hrs, usually from about 30 min to 12 hrs and more usually from about 1 hr to 6 hrs.

Following binding of probe and target, the resultant hybridization patterns of labeled probe may be visualized or detected in a variety of ways, with the particular manner of detection being chosen based on the particular label of the nucleic acid, where representative detection means include scintillation counting, autoradiography, fluorescence measurement, colorimetric measurement, light emission measurement and the like.

The method may or may not further comprise a non-bound label removal step prior to the detection step, depending on the particular label employed on the probe. For example, in homogenous assay formats a detectable signal is only generated upon specific binding of probe to target. As such, in homogenous assay formats, the hybridization pattern may be detected without a non-bound label removal step. In other embodiments, the label employed will generate a signal whether or not the probe is specifically bound to its is target. In such embodiments, the non-bound labeled probe is removed from the support surface. One means of removing the non-bound labeled probe is to perform the well known technique of washing, where a variety of wash solutions and protocols for their use in removing non-bound label are known to those of skill in the art and may be used. Alternatively, in those situations where the targets are entrapped in a separation medium in a format suitable for application of an electric field to the medium, the opportunity arise to remove non-bound labeled probe from the target by electrophoretic means.

The above methods can be varied to provide for multiplex analysis. For example, one can employ a plurality of different probe molecules that are each distinguishably labeled, e.g. with different fluorophores.

The above assays can be used to simultaneously determine both the expression level and the size of the target bound by the probe. The target expression level in the particular tissue being analyzed can be derived from the intensity of the detected signal. To ensure that an accurate level of expression is derived, a housekeeping gene of known expression level can also be detected, e.g. using a multiplex approach as described above, to provide for a control signal level in order to calibrate the detected probe signal. Since the pattern of target molecules of the array is arranged according to size, the position in the pattern to which the probe binds and where the probe is subsequently detected yield information regarding the size of the target molecule.

In yet another embodiment, RNA derived probe is labeled by a first label and then mixed with probe complementary to the size marker and labeled with a second label The probe mixture is then hybridized to the array and signals from the target and size probes are employed to calculate or determine the target size.

As such, the subject arrays find use in a variety of different gene expression analysis applications, including differential expression analysis of diseased and normal tissue, e.g. neoplastic and normal tissue; different tissues or subtypes; tissues and cells under different condition states, like predisposition to disease, age, exposure to pathogens or toxic agents, etc.; and the like.

Also provided are kits for performing binding assays using the subject arrays, where kits for carrying out differential gene expression analysis assays are preferred. Such kits according to the subject invention will at least comprise an array according to the subject invention, where the array may simply comprise a pattern of target molecules on a rigid planar support or be incorporated into a multiwell configuration, biochip configuration, or other configuration. The kits may further comprise one or more additional reagents for use in the assay to be performed with the array, where such reagents include: probe generation reagents, e.g. buffers, primers, enzymes, labels and the like; reagents used in the binding step, e.g. hybridization buffers; signal producing system members, e.g. substrates, fluorescent-antibody conjugates, etc.; and the like.

Finally, systems which incorporate the subject arrays, particularly the biochip an& multiwell configurations of the subject arrays, are provided, where the systems find use in high throughput gene expression analysis in which information regarding the expression level and a size of a gene in a tissue is desired. By the term "system" is meant the working combination of the enumerated components thereof, which components include the those components listed below. Systems of the subject invention will generally comprise the array, a fluid handling device capable of contacting the probe fluid and all reagents with the pattern of target molecules on the array and delivery and removing wash fluid from the array surface; a reader which is capable of providing identification of the location of positive probe target binding events and the intensity of the signal generated by such binding events; and preferably a computer means which capable of controlling the actions of the various elements of the system, i.e. when the reader is activated, when fluid is introduced and the like.

The following examples are offered by way of illustration and not by way of limitation.

Experimental

EXAMPLE 1

Generation and Use of Continuous RNAchip ps A. Gel Preparation and Electrophoresis The example provided below describes the use of a Macrophor sequencing system for the generation of an RNAchip according to the subject invention. However, the combination of any other vertical or horizontal gel electrophoresis equipment can be used to generate arrays according to the subject invention.

First, 5 ml of Bind-Silane solution (mixture of 20 ml absolute ethanol, 5 ml 10% acetic acid and 75 µl of γ-methacryloxy-propyl-trimethoxysilane (Bind-Silane, Pharmacia) is spread evenly over the top surface of a notch plate using lint-free tissue. The plate is allowed to dry for 2 min and then polished with a fresh lint-free tissue. The plate is rinsed with ethanol, and while it still wet the plate is polished with another tissue until it is dry. Using a lint-free tissue, 5 ml of Repel-Silane solution (Pharmacia) is spread over the entire top surface of the thermostatic plate and allowed to dry for 5 minutes. The plate is polished with a fresh lint-free tissue. The Repel-Silane treatment is then repeated. After the second polishing, the plate is rinsed with ethanol and while it is still wet, the plate is polished once more.

100 ml of gel solution is then prepared. To prepare the gel solution, 42 g of urea, 7.5 ml of 40% acrylamide (38% w/v acrylamide, 2% w/v N,N'-methylenebisacrylamide), 10 ml of 10xTBE buffer (1 M Tris-borate, 10 mM EDTA, pH 8.3) are combined. (The 3% acrylamide solution can be replaced by 3–5% of HydroLink gel (N,N'dimethylacrylamide/ethylene glycol dimethacrylate, AT Biochem)). The 99.2 ml remaining are made up with distilled water. The urea is dissolved and filtered through 0.45 $\mu$m pore size membrane. 0.8 ml of 10% ammonium persulphate solution and 90 $\mu$l of TEMED are then added to the mixture.

The mixture is then placed on the thermostatic plate on the MacroMould (Pharmacia) with the Repel-Silane treated surface facing upwards. The 0.4 mm spacers are positioned with clamps. The notched glass plates are placed with the notches to the opposite side of the support plate. The gel solution is then poured just in front of the notched glass plate while sliding it up the slope. When the nothes are 1 cm from the upper edge of the lower plate, the glass plates are clamped together, the comb is inserted, the comb clamp is fixed and polymerization is allowed to proceed for 1 hr.

To prepare the array, the comb clamp and comb is removed, the wells are washed and the glass plate assembly is installed into the Macrophor unit. The buffer vessels are filled with 1xTBE buffer and the gel is "pre-run" at 50° C. for 1 hr. For each sample preparation mix 1 $\mu$l of 1 mg/ml poly A+RNA with 1 $\mu$l of 10 M urea and 0.1 $\mu$l of 10xTBE buffer is heated at 70° C. for 2 min and loaded into the wells. The gel is run at 10–20 v/cm for 2 hours. Upon completion of the run, the notched plate is removed with its attached gel from the thermostatic plate and the RNA is cross-linked in the gel by UV irradiation in a Stratalinker (Stratagene) at 120 mJoules. The gel is washed in distilled water for 5 minutes and dried under vacuum in the incubator at 65° C. for 1 hour. The glass plate with the immobilized gel can be used directly for hybridization assay or can be incorporated into a biochip device as shown in FIGS. 2 or 3.

B. Labeling of DNA Probe by Cy3-dCTP.

Labeled DNA probe is prepared using the following protocol. 25 ng of double-stranded DNA probe is added to distilled $H_2O$ in a sterilized microcentrifuge tube to a final volume of 22 $\mu$l. As much as 50 ng of DNA can be added to the reaction mix if the probe is, being prepared for two hybridizations. 10 $\mu$l of 5×random hexamer primer solution (0.5 $\mu$g/ul $(dN)_6$) is then added, followed by mixing. The resultant-mixture is heated to 95–100° C. for 5 min and then placed on ice. The mixture is then spun briefly at room temperature to collect droplets formed by condensation. The following components are then added to the mixture: (1) 5 $\mu$l 10×Reaction buffer(0.4M Tris-HCl (pH 7.5), 0.1M $MgCl_2$, 50 mM DTT, 1 mg/ml BSA); (2) 2 $\mu$l each of dATP (0.5 mM), dTTP (0.5 mM), and dGTP (0.5 mM); (3) 0.5 $\mu$l dCTP (0.5 mM); (4) 0.5 mM Cy3-dCTP (0.5 mM) (Amersham);and (5) 1 $\mu$l [$\alpha$-$^{32}$P]dCTP. Next, 2 $\mu$l of T7 DNA polymerase (1 u/$\mu$l) is added to the reaction mixture. The mixture is then incubated at 37° C. for 20 min. 5 $\mu$l of 10×stop solution (0.1 M EDTA, 1 mg/ml glycogen) is then added to complete the reaction.

C. Purification of Cy3-labeled Probe by a Column Chromatography

To purify the Cy3-labelled DNA from unincorporated Cy3-labeled nucleotides and small (<0.1-kb) cDNA fragments, the following protocol is employed. A CHROMA SPIN-200 column (CLONTECH) is removed from refrigeration and warmed to room temperature for about 1 hour. The bottom cap is removed from the column, followed by removal of the top cap. The column is then placed into a 1.5-ml microcentrifuge tube. The water is allowed to drain through the column by gravity flow until the surface of the gel beads in the column matrix becomes visible. The collected water is then discarded. Next, the sample is applied to the center of the gel bed's flat surface and allowed to be fully absorbed into the resin bed. 25 $\mu$l of dd$H_2O$ are applied and allowed to completely drain out of the column. 200 $\mu$l of dd$H_2O$ are then applied and allowed to completely drain out of the column until there is no liquid left above the resin bed. The column is then transfered to a clean 1.5-ml microcentrifuge tube. 100 $\mu$l of dd$H_2O$ are added to the column and allowed to completely drain out of the column to collect the first fraction. Second, third and fourth fractions are collected in the same manner. The tubes with fractions 1–4 are placed in a scintillation counter and Cerenkov counts are obtained for each fraction by counting in the tritium channel. The fractions (usually fractions 2–3) which show highest Cerenkov counts are pooled.

D. Hybridization Cy3-labeled DNA Probe with RNA Chip

A solution of ExpressHyb (CLONTECH) and sheared salmon testes DNA (Sigma) is prepared as follows. First, 10 ml of ExpressHyb is prewarmed at 50–60° C. 1 mg of the sheared salmon testes DNA is heated at 95–100° C. for 5 min, and then chilled quickly on ice. The heat-denatured sheared salmon testes DNA is then mixed with prewarmed ExpressHyb. 5 ml of the resultant solution is introduced into inner chamber of an RNA chip (see e.g. FIGS. 2 and 3) and allowed to prehybridize for 30 min at 68° C. Cy3-labeled DNA probe (Step C, about 200 $\mu$l) is mixed with 5 $\mu$l (1 $\mu$g/$\mu$l) of human Cot-1 DNA denaturate at 95° C. for 2 min and then cooled in ice. The resultant mixture is added to 5 ml of ExpressHyb/salmon testes DNA solution and thoroughly mixed to produce the hybridization solution. The prehybridization solution in the RNA chip then replaced with the hybridization solution. Hybridization is allowed to proceed overnight at 68° C. The hybridization solution is then removed and discarded in an appropriate container. The bottle containing Wash Solution 1 (2×SSC, 1% SDS) prewarmed at 68° C., the peristaltic pump, the inlet port of RNA chip, the outlet port of RNA chip and the waste bottle are all connected by polyethylene tubing. The inner chamber of the RNA chip is washed by 200 ml of prewarmed Wash Solution 1 (2×SSC, 1% SDS) at the speed about 5 ml/min. Additional washes are performed by 100 ml of Wash Solution 2 (0.1×SSC, 0.5% SDS) prewarmed at 68° C. The RNA chip is then scanned in a Fluoroimager (Molecular Dynamics) to generate pattern of hybridization of the Cy3-labeled probe with RNA targets stably associated on the surface of the RNA chip.

EXAMPLE 2

Generation and use in Hybridization Assay of Discontinuous RNAchip

Step A. Separation of RNA by high performance liquid chromatography (RP-IP HPLC).

Size fractionation of poly A+RNA is accomplished by reverse-phase ion-pair high performance liquid chromatography ( RP-IP HPLC) as follows:

1 mg of poly A+RNA is injected into a DNASep column (Serasep Inc, San Jose; Transgenomics) and separated using BioCAD700E Perfusion Chromatography Workstation (PerSeptive Biosystem, Framington) in the linear gradient of 5%–80% of acetonitryl containing 0.1M of trimethylammonium ion. 100 polyA+RNA fractions corresponding to sizes of RNA between 200 nucleotides to about 12,000 nucleotides with the differences in average size of RNAs in each fraction about 100–200 nucleotides are collected, dried under vacuum and dissolved in 20 µl of denaturing buffer (0.1 MOPS (pH 7.0), 1 mM EDTA, 20% formaldehyde and 50% formamide).

Step B. Immobilization of RNA fractions on the Surface of RNA Chip

The RNA fractions generated at Step A are then transferred to a 384-well plate, incubated at 65° C. for 20 min and loaded on glass plate using 384 pin tool and Biomek 2000 (Beckman) robot. Each of 200 fractions of each poly A+RNA are applied in consecutive order in the form of a lane which imitates the size distribution of the RNAs generated in the course of gel electrophoresis. In parallel the RNA size marker fraction is applied in separate lane which allows subsequent determination of the size of RNAs revealed in hybridization assay. Immobilized RNA are crosslinked with the support by UV irradiation in a Stratalinker (Stratagene) at 120 mJoules, the plate is washed in distilled water for 5 minutes and dried under vacuum in the incubator at 65° C. for 1 hour. The glass plate with RNA fractions is used directly for hybridization assay or can be incorporated into the biochip device as shown in FIG. 2 or 3. The RNA chip can be used then in a hybridization assay as described above.

EXAMPLE 3

Preparation and Use of RNA Chip

A. Pin Spotting of Poly A+RNAs on a Solid Support

A. 1 Dot blot format

A set of different poly A+RNAs, usually between 8 and 100, are spotted on a solid glass support. The poly A+RNAs are stably associated with the glass surface through covalent binding. Several methods may be employed for the attachment of nucleic acids, i.e. DNA or RNA, to glass. For example, aliphatic amino groups are introduced to the surface of glass slides by reaction with aminopropyl silane. Poly A+RNAs pretreated with 10 M sodium isothiocyanate (NaNCS) solution (1:1) are then pin spotted onto the aminopropyl modified glass surface by a Biomek 2000 (Beckmann) robot. The binding occurs through aminoreactive phenylisothiocyanate groups The poly A+RNAs are photo-crosslinked to further ensure stable association with the surface of the glass support. In addition, the glass slides are incubated for 2 hours at 80° C. Alternatively, an amino derivatized glass surface is; coupled to p-phenylenediisothiocyanate (PDC) to convert the amino groups to aminoreactive phenylisothiocyanate groups. Nucleic acids are then reacted with their amino grouse and the second isothiocyanate group in PDC to yield surface bound DNA or RNA. The reaction is carried out in 0.5-M sodium carbonate buffer, pH: 9.1. After UV-crosslinking either aminopropyl modified or PDC modified glass slides are washed in ddH$_2$O at 95° C., for5 min. To avoid background signals after hybridization the glass slides are blocked for 15 min with 100 mM glycine solution. Then glass slides are rinsed with ddH$_2$O and ethanol. After incubation for 15 min at 37° C. the slides are ready for use in hybridization experiments.

A. 2 Micro Northern format

Poly A+mRNA is size fractionated by denaturing high performance liquid chromatography (DHPLC) using different approaches: (i) reverse-phase ion-pair HPLC (RP-IP HPLC), (DNASep, Transgenomics, San Jose); (ii) and anion-exchange HPLC (G-DNA-PW, TosoHaas). 1 mg of poly A+RNA is separated using the Transgenomics WAVE HPLC System. For RP-IP HPLC different ion-pair solvents are used, e.g. triethylammoniumacetate (TEAA), trimethylammoniumacetate (TMAA), tetramethylammoniumbromide (TMAB), tetraethylammoniumbromide (TEAB), tetrapropylammoniumbromide (TPAB), tetrabutylammoniumbromide (TBAB), and the like. By using an isocratic acetonitrile gradient (16–17%) in TEAA poly A+mRNA, 50–3,000 nucleotides can be fractionated. Larger RNAs in the size range from 3,000–12,000 nucleotides are separated by denaturing anion-exchange chromatography. RNA is denatured by incubation at 65° C. for 15 min. The fractionation is carried out in 20 mM Tris/HCl buffer, pH: 8.0 using a 30 min linear gradient from either 0.5–0.75 M sodium chloride (NaCl) or from 0.17–0.26 M sodium acetate (NaAc). The flow rate is 1.0 ml/min. The column temperature is 60° C. Alternatively, prior to bonding RNA is chemically denatured with glyoxal as described in Maniatis, et al. In this case, a 10 mM 3-morpholinopropanesulfoinic acid (MOPS) buffer, pH: 7.8 is used. Between 50–100 RNA fractions with differences in average size of about 100–200 nucleotides are collected, precipitated with ethanol, dried under vacuum, and dissolved in RNAse free water. In the case of aminopropyl modified glass supports, RNAs are pretreated with 5 M sodium isothiocyanate (NaNCS) solution and pin-spotted on a solid support as described under A.1. In the case of PDC modified glass supports, RNAs are preincubated with 0.5 M sodium carbonate, pH: 9.1, as described under A.1.

Labeling of DNA Probe

Oligonucleotide primers, 20–40 base pairs in length, are designed against each of the selected genes used as DNA probes. PCR reactions are carried out to amplify 200–800 bp cDNA probes. The cDNAs are radiolabeled, i.e. with [$^{32}$P] dATP or [$^{32}$P]dCTP as described in CLONTECH's User Manual, standard procedure, Clontech Laboratories-Inc., Palo Alto, Calif.). Alternatively, the cDNAs are non-radioactively labeled with either fluorescence markers or with metal particles, i.e. gold, silver etc. (available from Genicon, San Diego, Calif.), bound to biotin (for detection via light scattering).

Fluorescein-labeled DNA probe is prepared as follows. 25 ng of double stranded DNA probe is dissolved in a final volume of 22 µl ddH$_2$O. 10 µl of random hexamer primer solution (0.5 µg/µl) is added followed by mixing. The resultant mixture is heated at 95–100° C. for 5 min. and then placed on ice. The following components are then added to the resultant mixture: 5 µl of 10×Reaction buffer (0.4 M Tris-HCl, pH:7.5 , 0.1 M MgCl$_2$, 50 mM DTT, 1 mg/ml BSA); 2 µl each of dATP (0.5 mM), dTTP (0.5 mM) and dGTP (0.5 mM); 0.5 µl of dCTP (0.5 mM); 0.5 µl of Cy3-dCTP (0.5 mM) or Cy5-dCTP (Amersham); and 1 µl of [α-$^{32}$P]dCTP. 2 µl of T7 DNA polymerase (1 U/µl) is then added to the reaction mixture. The mixture is then incubated at 37° C. for 20 min. 5 µl of 10×stop solution (0.1 M EDTA; 1 mg/ml glycogen) is then added to complete the reaction.

Unincorporated radio-labeled or fluorescein-labeled nucleotides are removed by size exclusion chromatography using the following procedure: (1) ChromaSpin-200 column (CLONTECH) is removed from a refrigerator and warmed for about 1 hour. The column is then inverted several times to completely resuspend the gel matrix. The bottom cap is removed from the column followed by removal of the top cap. The column is placed into a 1.5 ml microcentrifuge tube. The water is allowed to drain through the column by gravity flow until the surface of the gel beads in the column matrix become visible. The collected water is discarded and purification proceeds as follows. The sample is applied to the center of the gel bed's flat surface and allowed to be fully absorbed into the resin bed. 25 $\mu$l of ddH$_2$O are applied and the water is allowed to completely drain out of the column. 200 $\mu$l of ddH$_2$0 is applied and the buffer is allowed to completely drain out of the column until there is no liquid left above the resin bed. The column is transferred to a clean 1.5 ml microcentrifuge tube. 100 $\mu$l of ddH$_2$O is added to the column and allowed to completely drain out of the column to collect the first fraction. Additional fractions are collected in the same manner. Cerenkov counts are then taken for the resultant fractions, followed by pooling of the fractions (usually fractions 2 and 3) which show the highest Cerenkov counts, C. Hybridization, X-ray Detection or Fluorescence Detection The glass slides with immobilized poly A+RNAs produced as described above are incubated with 5 ml of CLONTECH's "ExpressHybridization" solution (Clontech, Palo Alto, Calif.) mixed with either radiolabeled or fluorescein-labeled cDNAs. The hybridization temperature is 50° C. Incubation occurs overnight. The glass slides are washed twice with 2×SSC, 0.1% SDS solution for 10 min. at room temperature, once with 1×SSC, 0.1% SDS solution for 5 min. at 68° C., and once with 0.1×SSC for 5 min. at room temperature. Finally, the glass slides are rinsed with sterile filtered water for about 1 min. Hybridization signals are detected using either a phosphorimager in the case of emission of radioactive signals or a fluoroimager (Molecular Dynamics) in the case of emission of fluorescent signals.

It is evident from the above results and discussion that the subject arrays provide for improved methodologies in gene expression analysis applications, particularly in those applications in which both expression level and size information of the target are desired. The subject arrays are capable of being premade and then used in assays at a later date and by a different user, thereby saving the assay performer from having to go through the preparation of the array at the time of use. Since the subject arrays can be pre-prepared, they can be mass produced under uniform specifications, thereby assuring comparability of results obtained using the subject devices. Furthermore, since the subject arrays comprise a solid support, they are particularly suited for use in high throughput analyses and with automated devices, such as fluid handling devices, readers and the like. Finally, the subject arrays can be fabricated in such a way as to readily usable with standard detection devices currently employed by those in the relevant fields.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for detecting a binding event between a probe and target compound, said method comprising:

contacting a probe comprising solution with an array of heterogenous ribonucleic acid targets stably associated with a surface of a rigid solid support, wherein said heterogenous ribonucleic acid targets are arranged according to size; and detecting a binding event between at least one of said heterogenous ribonucleic acid targets and said probe.

2. The method according to claim 1, wherein said probe is labeled and said detecting, comprises detecting the presence of said label.

3. The method according to claim 2, wherein said label is selected from the group consisting of isotopic, fluorescent and enzymatic labels.

4. The method according to claim 1, wherein said method further comprises washing said support of unbound probe prior to said detecting.

5. A kit for use in a method of detecting a binding event between a probe and target, said kit comprising:

an array of heterogenous ribonucleic acid targets stably associated with a surface of a rigid solid support, wherein said heterogenous ribonucleic acid targets are arranged according to size.

6. The kit according to claim 5, wherein said kit further comprises one or more members of a signal producing system.

7. The kit according to claim 5, wherein said kit further comprises at least one buffer medium.

8. A method for producing an array of heterogenous ribonucleic acid targets stably associated with a surface of a rigid solid support, wherein said heterogenous ribonucleic acid targets are arranged according to size, said method comprising:

separating a plurality of heterogenous ribonucleic acid targets according to size; and stably associating said size separated heterogenous ribonucleic acid targets with a surface of a rigid solid support.

9. The method according to claim 8, wherein said separating is performed by introducing said plurality of ribonucleic acid targets into a separation medium and applying an electric field to said medium.

10. An array of a plurality of heterogeneous ribonucleic acid samples, wherein said plurality of ribonucleic acid samples are:

(a) stably associated with a surface of a rigid support;
(b) isolated from at least one biological source; and
(c) arranged on said rigid support according to size.

11. The array of claim 10, wherein said plurality of heterogeneous ribonucleic acid samples are comprised of messenger RNA.

12. The array of claim 10, wherein said plurality of heterogeneous ribonucleic acid samples are covalently bound to said surface of said solid support.

13. The array of claim 10, wherein said plurality of heterogeneous ribonucleic acid samples are arranged in a continuous size format.

14. The array of claim 10, wherein said plurality of heterogeneous ribonucleic acid samples are arranged in a discontinuous size format.

15. The array of claim 10, wherein said array comprises at least five heterogeneous ribonucleic acid samples.

16. A method of making an array of a plurality of heterogeneous ribonucleic acid samples comprising the steps of:

isolating ribonucleic acid samples from a biological source;
  fractionating said ribonucleic acid samples by size;
  positioning said fractionated ribonucleic acid samples on a rigid support according to size; and
  stably associating said positioned, fractionated RNA to said rigid support.

17. The method of claim 16, wherein said fractionated ribonucleic acid samples are messenger ribonucleic acids.

18. The method of claim 16, wherein said fractionated ribonucleic acids are positioned according to increasing size.

19. The method of claim 18, wherein said fractionated ribonucleic acids are positioned in a continuous size format.

* * * * *